(12) United States Patent
Aria et al.

(10) Patent No.: US 8,764,681 B2
(45) Date of Patent: Jul. 1, 2014

(54) SHARP TIP CARBON NANOTUBE MICRONEEDLE DEVICES AND THEIR FABRICATION

(71) Applicant: California Institute of Technology, Pasadena, CA (US)

(72) Inventors: Adrianus I. Aria, Pasadena, CA (US); Bradley Lyon, Arcadia, CA (US); Morteza Gharib, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 13/715,604

(22) Filed: Dec. 14, 2012

(65) Prior Publication Data

US 2013/0178722 A1    Jul. 11, 2013

Related U.S. Application Data

(60) Provisional application No. 61/570,688, filed on Dec. 14, 2011.

(51) Int. Cl.
*A61B 5/00*    (2006.01)

(52) U.S. Cl.
USPC ............................. 600/573; 977/842; 977/855

(58) Field of Classification Search
USPC ................................... 977/842, 855; 600/573
See application file for complete search history.

(56) References Cited

U.S. PATENT DOCUMENTS

| | | | |
|---|---|---|---|
| 3,964,482 A | 6/1976 | Gerstel et al. |
| 5,457,041 A | 10/1995 | Ginaven et al. |
| 6,256,533 B1 | 7/2001 | Yuzhakov et al. |
| 6,334,856 B1 | 1/2002 | Allen et al. |
| 6,379,324 B1 | 4/2002 | Gartstein et al. |
| 6,471,903 B2 | 10/2002 | Sherman et al. |
| 6,503,231 B1 | 1/2003 | Prausnitz et al. |
| 6,533,949 B1 | 3/2003 | Yeshurun et al. |
| 6,720,547 B1 | 4/2004 | Rajadhyaksha et al. |
| 6,749,792 B2 | 6/2004 | Olson |
| 6,924,335 B2 | 8/2005 | Fan et al. |
| 7,037,562 B2 | 5/2006 | Jimenez |
| 7,097,776 B2 | 8/2006 | Govinda Raju |
| 7,160,620 B2 | 1/2007 | Huang et al. |
| 7,183,003 B2 | 2/2007 | Leu et al. |
| 7,235,442 B2 | 6/2007 | Wang et al. |
| 7,291,396 B2 | 11/2007 | Huang et al. |
| 7,393,428 B2 | 7/2008 | Huang et al. |
| 7,396,477 B2 | 7/2008 | Hsiao |
| 7,438,844 B2 | 10/2008 | Huang et al. |
| 7,491,628 B2 | 2/2009 | Noca et al. |

(Continued)

FOREIGN PATENT DOCUMENTS

| | | |
|---|---|---|
| JP | 2006114265 | 4/2006 |
| JP | 2006164835 | 6/2006 |

(Continued)

OTHER PUBLICATIONS

EP, 10710690.8—First Office Action, Jul. 19, 2012.

(Continued)

*Primary Examiner* — Max Hindenburg

(74) *Attorney, Agent, or Firm* — One LLP

(57) ABSTRACT

Carbon nanotube needles and needle arrays are described in which the precursor pillars are etched by oxygen plasma treatment to provide tapered and/or sharp-tip needles. Processes, products by process, and devices incorporating the sharp-tip needles are further described.

16 Claims, 2 Drawing Sheets

(56) References Cited

U.S. PATENT DOCUMENTS

| | | | |
|---|---|---|---|
| 7,569,425 | B2 | 8/2009 | Huang et al. |
| 7,611,651 | B2 | 11/2009 | Huang et al. |
| 7,955,644 | B2 | 6/2011 | Sansom et al. |
| 8,043,250 | B2 | 10/2011 | Xu |
| 8,048,017 | B2 | 11/2011 | Xu |
| 8,062,573 | B2 | 11/2011 | Kwon |
| 8,257,324 | B2 | 9/2012 | Prausnitz et al. |
| 2002/0155737 | A1 | 10/2002 | Roy et al. |
| 2003/0069548 | A1 | 4/2003 | Connelly et al. |
| 2003/0180472 | A1 | 9/2003 | Zhou et al. |
| 2005/0011858 | A1 | 1/2005 | Kuo et al. |
| 2005/0029223 | A1 | 2/2005 | Yeshurun et al. |
| 2005/0127351 | A1 | 6/2005 | Tolt |
| 2005/0136248 | A1 | 6/2005 | Leu et al. |
| 2005/0157386 | A1 | 7/2005 | Greenwald et al. |
| 2005/0167647 | A1 | 8/2005 | Huang et al. |
| 2005/0171480 | A1 | 8/2005 | Mukerjee et al. |
| 2005/0220674 | A1 | 10/2005 | Shafirstein et al. |
| 2005/0230082 | A1 | 10/2005 | Chen |
| 2005/0245659 | A1 | 11/2005 | Chen |
| 2006/0030812 | A1 | 2/2006 | Golubovic-Liakopoulos et al. |
| 2006/0057388 | A1 | 3/2006 | Jin et al. |
| 2006/0073332 | A1 | 4/2006 | Huang et al. |
| 2006/0073712 | A1 | 4/2006 | Huang et al. |
| 2006/0084942 | A1 | 4/2006 | Kim et al. |
| 2006/0086689 | A1 | 4/2006 | Raju |
| 2006/0093642 | A1 | 5/2006 | Ranade |
| 2006/0118791 | A1 | 6/2006 | Leu et al. |
| 2006/0184092 | A1 | 8/2006 | Atanasoska et al. |
| 2006/0226016 | A1 | 10/2006 | S/O Govinda Raju et al. |
| 2006/0231970 | A1 | 10/2006 | Huang et al. |
| 2007/0004081 | A1 | 1/2007 | Hsiao |
| 2007/0053057 | A1 | 3/2007 | Zust et al. |
| 2007/0059864 | A1 | 3/2007 | Huang et al. |
| 2007/0066934 | A1 | 3/2007 | Etheredge, III et al. |
| 2007/0099311 | A1 | 5/2007 | Zhou et al. |
| 2007/0207182 | A1 | 9/2007 | Weber et al. |
| 2007/0276330 | A1 | 11/2007 | Beck et al. |
| 2008/0009800 | A1 | 1/2008 | Nickel |
| 2008/0081176 | A1 | 4/2008 | Huang et al. |
| 2008/0145616 | A1 | 6/2008 | Gharib et al. |
| 2008/0269666 | A1 | 10/2008 | Wang et al. |
| 2009/0032496 | A1 | 2/2009 | Yao et al. |
| 2009/0118662 | A1 | 5/2009 | Schnall |
| 2010/0196446 | A1 | 8/2010 | Gharib et al. |
| 2010/0247777 | A1 | 9/2010 | Nikolaev et al. |
| 2011/0233779 | A1 | 9/2011 | Wada et al. |
| 2011/0250376 | A1 | 10/2011 | Aria et al. |
| 2012/0021164 | A1 | 1/2012 | Sansom et al. |
| 2012/0058170 | A1 | 3/2012 | Gharib et al. |

FOREIGN PATENT DOCUMENTS

| | | |
|---|---|---|
| TW | 253 898 | 4/2006 |
| TW | 256 877 | 6/2006 |
| WO | WO96/21938 | 7/1996 |
| WO | WO2006/041535 | 4/2006 |
| WO | WO2010/087971 | 8/2010 |
| WO | WO 2010/120564 A2 | 10/2010 |
| WO | WO 2013/090844 A1 | 6/2013 |

OTHER PUBLICATIONS

PCT, PCT/US2007/015754 IPRP, Feb. 11, 2010.
PCT, PCT/US2007/015754 ISR/Written Opinion, Jan. 25, 2010.
PCT, PCT/US2008/012641 ISR/Written Opinion, Feb. 12, 2009.
PCT, PCT/US2008/012641 IPRP, May 20, 2010.
PCT, PCT/US2010/000243 ISR/Written Opinion, Nov. 11, 2010.
PCT, PCT/U52010/000243 IPRP, Aug. 2, 2011.
U.S. Appl. No. 12/657,862 Non-Final Office Action, Mar. 14, 2012.
U.S. Appl. No. 12/657,862 Final Office Action, Sep. 7, 2012.
Ajayan, P., et al., 1994, "Aligned carbon nanotube arrays formed by cutting a polymer resin-nanotube composite," Science 265(5176): 1212-1214.
Barber, A. H., et al., "Static and dynamic wetting measurements of single carbon nanotubes," Physical review letters 92(18): 186103, 2004.
Boldor, D., et al., 2008, "Temperature measurement of carbon nanotubes using infrared thermography," Chemistry of materials 20(12): 4011-4016.
Boo, F-E, et al., "Electrochemical nanoneedle biosensor based on multiwall carbon nanotube," Analytical chemistry 78(2): 617-620, 2006.
Borca-Tasciuc, T., et al., 2007, "Anisotropic thermal diffusivity characterization of aligned carbon nanotube-polymer composites," Journal of Nanoscience and Nanotechnology 7(4): 1581-1588.
Bronikowski, M. J., Longer nanotubes at lower temperatures: The influence of effective activation energies on carbon nanotube growth by thermal chemical vapor deposition. Journal of Physical Chemistry C, 2007. 111 (48): p. 17705-17712.
Choi, T., et al., 2005, "Measurement of thermal conductivity of individual multiwalled carbon nanotubes by the 3-omega method," Applied physics letters 87(1): 013108.
Crabtree, G. W., et al., 2007, "Solar energy conversion," Physics today 60(3): 37-42.
Correa-Duarte, M. A., et al., "Nanoengineered polymeric thin films by sintering CNT-coated polystyrene spheres," Small 2 (2): 220-224, 2006.
Creel, C.J., et al., Arterial paclitaxel distribution and deposition. Circulation Research, 2000. 86(8): p. 879-884.
Dai, L., et al., "Functionalized surfaces based on polymers and carbon nanotubes for some biomedical and optoelectronic applications," Nanotechnology, vol. 14, No. 10, Oct. 1, 2003, pp. 1084-1097.
Falvo, M. R., et al., 1997, "Bending and buckling of carbon nanotubes under large strain," Nature 389(6651): 582-584.
Fan, S. S., et al., 1999, "Self-oriented regular arrays of carbon nanotubes and their field emission properties," Science 283(5401): 512-4.
Firkowska, I. et al., "Highly ordered MWNT-based matrixes: topography at the nanoscale conceived for tissue engineering," Langmuir 22(12): 5427-5434, 2006.
Frank, S., et al., 1998, "Carbon nanotube quantum resistors," Science 280(5370): 1744-1746.
Hinds, B. J., et al., 2004, "Aligned multiwalled carbon nanotube membranes," Science 303(5654): 62-5.
Huang, H., et al., 2005, "Aligned carbon nanotube composite films for thermal management," Advanced materials 17(13): 1652.
Huang, X., et al., "Inherent-opening-controlled pattern formation in carbon nanotube arrays," Nanotechnology 18 (2007) 305301 (6pp).
Huber, C.A., et al., "Nanowire array composites," Science 263(5148): 800-802, 1994.
Iijima, S., 1991, "Helical microtubules of graphitic carbon," Nature 354 (6348): 56-58.
Jin, L., et al., "Alignment of carbon nanotubes in a polymer matrix by mechanical stretching," Applied physics letters 73(9): 1197-1199, 1998.
Jung, Y. J., et al., "Aligned carbon nanotube-polymer hybrid architectures for diverse flexible electronic applications," Nano letters 6(3): 413-418, 2006.
Kam, N. W. S., et al., 2005, "Carbon nanotubes as multifunctional biological transporters and near-infrared agents for selective cancer cell destruction," Proceedings of the National Academy of Sciences of the United States of America 102(33): 11600-11605.
Kim, P., et al., 2001, "Thermal transport measurements of individual multiwalled nanotubes," Physical review letters 87(21): 215502.
Lahiff, E., et al., "Selective positioning and density control of nanotubes within a polymer thin film," Nano letters 3(10): 1333-1337, 2003.
Lee, J. U., 2005, "Photovoltaic effect in ideal carbon nanotube diodes," Applied physics letters 87(7): 073101.
Li, W. Z., et al., "Large-scale synthesis of aligned carbon nanotubes," Science 274(5293): 1701-1703, 1996.
Mamedov, A. A., et al., "Molecular design of strong single-wall carbon nanotube/polyelectrolyte multilayer composites," Nature materials 1(3): 190-194, 2005.

(56) References Cited

OTHER PUBLICATIONS

Melechko, A. V., et al., "Vertically aligned carbon nanofibers and related structures: Controlled synthesis and directed assembly," Journal of applied physics 97(4): 041301, 2005.

Morjan, R. E., et al., "High growth rates and wall decoration of carbon nanotubes grown by plasma-enhanced chemical vapour deposition," Chemical physics letters 383 (3-4): 385-390, 2004.

Nerushev, O. A., et al., "The temperature dependence of Fe-catalysed growth of carbon nanotubes on silicon substrates," Physica. B, Condensed matter 323(1-4): 51-59, 2002.

Noca, F., et al., 2007, "Nanowicks," NASA Tech Briefs 31(10): 32-3.

Raravikar, N. R., et al., 2005, "Synthesis and characterization of thickness-aligned carbon nanotube-polymer composite films," Chemistry of materials 17(5): 974-983.

Raravikar, N. R., et al., "Embedded carbon-nanotube-stiffened polymer surfaces," Small 1(3): 317-320, 2005.

Ren, Z. F., et al., "Synthesis of large arrays of well-aligned carbon nanotubes on glass," Science 282(5391): 1105-1107, 1998.

Sansom, E. B., et al., 2008, "Controlled partial embedding of carbon nanotubes within flexible transparent layers," Nanotechnology 19(3): 035302.

Sansom, E. B., "Experimental Investigation on Patterning of Anchored and Unanchored Aligned Carbon Nanotube Mats by Fluid Immersion and Evaporation," Ph. D. Thesis, California Institute of Technology, Pasadena, California, 2007.

Scheller, B., et al., Paclitaxel balloon coating, a novel method for prevention and therapy of restenosis. Circulation, 2004. 110(7): p. 810-814.

Sethi, S., et al., 2008, "Gecko-inspired carbon nanotube-based self-cleaning adhesives," Nano letters 8(3): 822-825.

Sinha, N., et al, "Carbon Nanotubes for Biomedical Application," IEEE Transactions on Nanobioscience, IEEE Service Center, Piscataway, NY, vol. 4, No. 2, Jun. 1, 2005, pp. 180-195.

Suh, J. S., et al., "Highly ordered two-dimensional carbon nanotube arrays," Applied physics letters 75(14): 2047-2049, 1999.

Tian, B. Z., et al., 2007, "Coaxial silicon nanowires as solar cells and nanoelectronic power sources," Nature 449(7164): 885-8.

Wagner, N. D., et al., "Stress-induced fragmentation of multiwall carbon nanotubes in a polymer matrix,"Applied physics letters 72(2): 188-190, 1998.

Wong, E. W., et al., "Nanobeam mechanics: Elasticity, strength, and toughness of nanorods and nanotubes," Science 277(5334): 1971-1975, 1997.

Xie, X. L., et al., "Dispersion and alignment of carbon nanotubes in polymer matrix: A review," materials science & engineering. R, Reports 49(4): 89-112, 2005.

Xu, Z., et al., 2006, "Multiwall carbon nanotubes made of monochirality graphite shells," Journal of the American Chemical Society 128(4): 1052-1053.

Yang, Z. P., et al., 2008, "Experimental observation of an extremely dark material made by a low-density nanotube array," Nano letters 8(2): 446-451.

Yurdumakan, B., et al., 2005, "Synthetic gecko foot-hairs from multiwalled carbon nanotubes," Chemical Communications 30: 3799-3801.

Zhao, L., et al., "Porous silicon and alumina as chemically reactive templates for the synthesis of tubes and wires of SnSe, Sn, and $SnO_2$," Angewandte Chemie 45(2): 311-315, 2006.

Zhou, J., et al., 2006, "Flow conveying and diagnosis with carbon nanotube arrays," Nantechnology 17(19): 4845-4853.

WO, PCT/US2012/069941 ISR, Feb. 21, 2013.

Aria, A.I., et al., "Reversible Tuning of the Wettability of Carbon Nanotube Arrays: The Effect of Ultraviolet/Ozone and Vacuum Pyrolysis Treatments", Langmuir, 2011, vol. 27, pp. 9005-9011.

Bronikowski, M.J., "CVD growth of carbon nanotube bundle arrays", Carbon, 2006, vol. 44, pp. 2822-2832.

Davis, S. P., et al., "Insertion of microneedles into skin: measurement and prediction of insertion force and needle fracture force", Journal of Biomechanics, 2004, vol. 34, pp. 1155-1163.

Haq, M.I., et al., "Clinical administration of microneedles: skin puncture, pain and sensation", Biomedical Microdevices, 2009, vol. 11, pp. 35-47.

Hart, A.J., et al., "Rapid Growth and Flow-Mediated Nucleation of Millimeter-Scale Aligned Carbon Nanotube Structures from a Thin-Film Catalyst", J. Phys, Chem, B, 2006, vol. 110, pp. 8250-8257.

Kaushik, S., et al., "Lack of Pain Associated with Microfabricated Microneedles", Anesthesia & Analgesia, 2001, vol. 92, pp. 502-504.

Roxhed, N., et al., "Painless Drug Delivery Through Microneedle-Based Transdermal Patches Featuring Active Infusion", IEEE Transactions on Biomedical Engineering, 2008, vol. 55, No. 3, pp. 1063-1071.

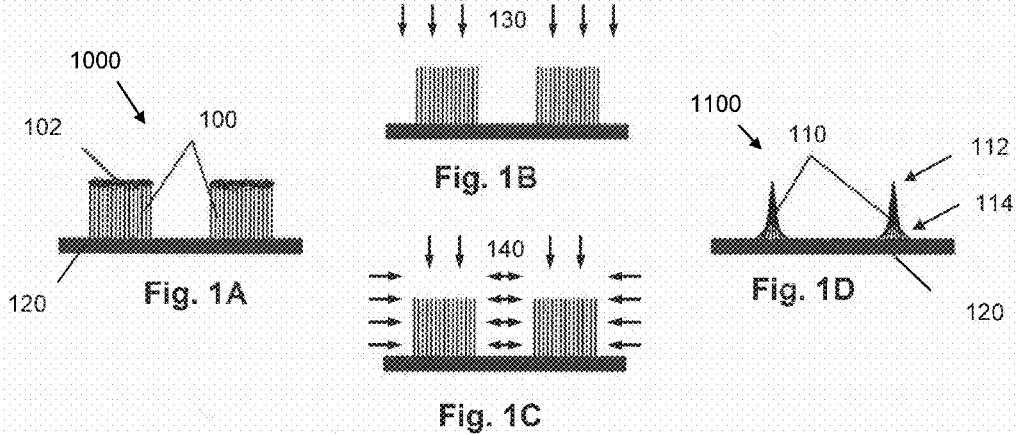
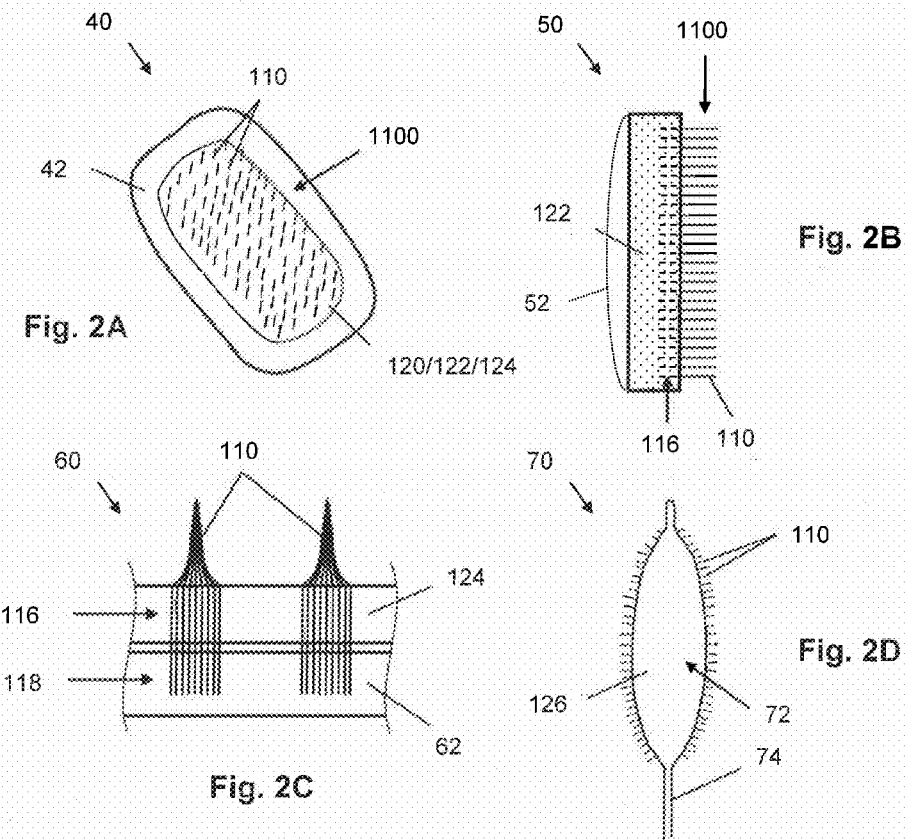

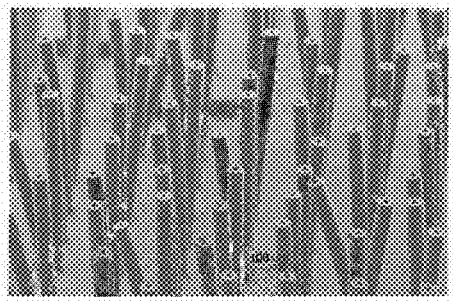
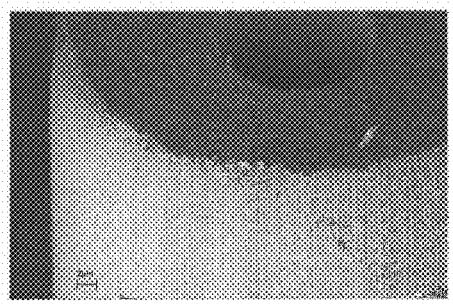
Fig. 3A					Fig. 3B
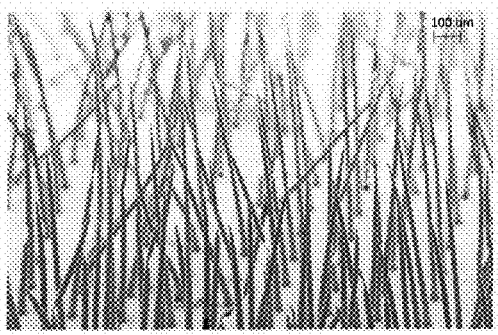
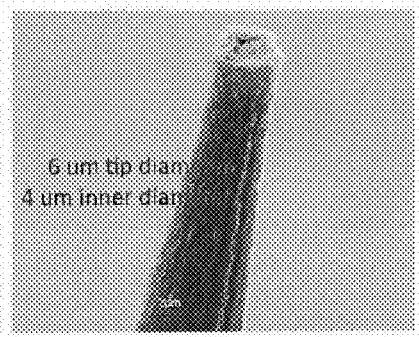
Fig. 4A					Fig. 4B
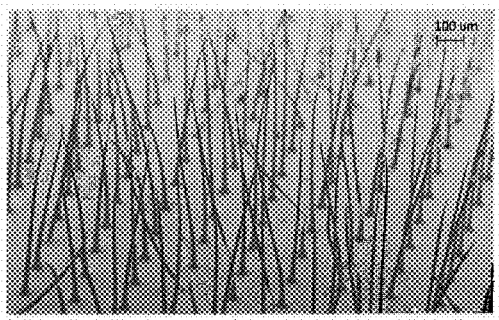
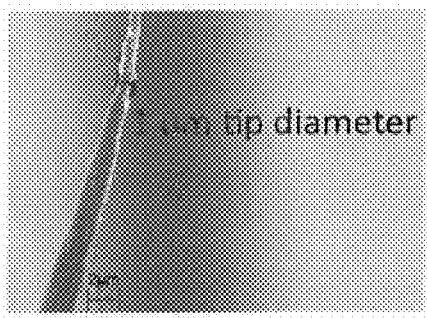
Fig. 5A					Fig. 5B

SHARP TIP CARBON NANOTUBE MICRONEEDLE DEVICES AND THEIR FABRICATION

RELATED APPLICATIONS

This filing claims the benefit of U.S. Provisional Patent Application Ser. No. 61/570,688 filed 14 Dec. 2011, which application is incorporated by reference herein in its entirety for all purposes.

FIELD

This filing relates to micro- and/or nano-scale needles (herein after simply referred to as microneedles), especially carbon nanotube (CNT) microneedles, microneedle arrays and microneedle array-type devices.

BACKGROUND

In the last few decades, the development of new drugs that have much more potency has been a primary focus in the pharmaceutical field. However, the administration of such drugs has been limited due to poor absorption and enzymatic degradation in the gastrointestinal tract as well as painful delivery using intravascular injection. One feasible solution to solve these problems is by administering those drugs across the skin using a patch, although its therapeutic rates are very limited due to skin permeability. In recent years, substantial effort has been spent to overcome this difficulty by incorporating skin permeation enhancer, electric field, ultrasound, and microneedles in the drug delivery systems. Among these approaches, the use of microneedles appears most promising since they can provide holes to bypass the stratum corneum of a patient's skin with little or no pain.

Microneedles, especially when arranged in arrays, find use in obtaining biological fluid samples and for delivering drugs, agents, formulations or biological molecules across biological tissue barriers. The microneedles used for delivering one or more compounds may be categorized as luminal or dissolvable. Dissolvable microneedles include a polymer tip that dissolves when in contact with body fluid to deliver a drug, vaccine inoculation, or other therapeutic agent. As the designation implies, luminal microneedles are bodies that include a lumen therein.

The lumen in this class of microneedle may be used to deliver compounds (especially in connection with various reservoir means such as described in U.S. Pat. No. 3,964,482 or 8,257,324). Alternatively, the lumen may be used for analyte collection, in which case, an array of microneedles may be combined with analyte measurement systems to provide a minimally invasive fluid retrieval and analyte sensing system such as described in U.S. Pat. No. 6,749,792. Notable analytes of interest obtained from biological fluids include glucose and cholesterol.

Microneedles are sometimes made from stainless steel or other metals. Metal needles are subject to numerous disadvantages. Some of these include the manufacturing complexities associated with wire drawing, grinding, deburring, and clean-up steps of the manufacturing process. Further, impurities in the metals can cause oxidation and deterioration of the needles. Further examples of microneedle fabrication approaches include employing photolithography and electroplating. Ultimately, silicon-based or stainless steel-based microneedles are not attractive due to their high material and fabrication cost.

Other microneedles are fabricated employing micro-replication techniques, such as injection molding of a plastic material or the like. Such approaches enable a degree of design flexibility and cost savings.

However, the resulting products of all of the aforementioned fabrication techniques fail to offer many of the advantages associated with microneedles and microneedle arrays fabricated from carbon nanotubes (CNTs). CNT-based microneedles have unmatched advantages due to their exceptional mechanical properties and simple fabrication process. Regarding ease of fabrication, they may be produced in large quantity by self-assembly to form a nanotube "carpet" of columns or pillars through chemical vapor deposition (CVD) or such other processes as described in U.S. Pat. No. 7,491,628 or US Publication Nos. 2003/0180472, 2008/0145616 or 2010/0247777. As to physical properties important to microneedle fabrication (aside from size in a relevant range), CNT-based microneedles offer superb column strength (i.e., an ability to withstand a compression load of at least 80 MPa), flexibility (as a measure of toughness against inadvertent damage in handling), and high aspect ratio.

In order to achieve such advantages, however, the so-called carpet of CNT pillars must be processed further in order to configure a workable microneedle array. Suitable processing techniques and the resulting array structures are described in U.S. Pat. No. 7,955,644 and US Publications 2010/0196446, 2012/0021164 and 2012/0058170—all assigned to California institute of Technology (the assignee hereof) and all (together with their foreign counterparts) incorporated herein by reference in their entireties for all purposes. Moreover, such arrays may be further processed to produce superhydrophobic CNT arrays as described in US Publication No. 2011/0250376 (also to the assignee hereof and incorporated by reference herein in its entirety) through vacuum pyrolysis.

Different forms of improvement to such devices (e.g., as described in any U.S. Pat. No. 7,955,644 and US Publications 2010/0196446, 2011/0250376, 2012/0021164 and 2012/0058170) or other CNT microneedles or microneedle arrays are described herein.

SUMMARY

Namely, CNT microneedle and microneedle array fabrication is contemplated in which the starting-material carbon nanotube pillars are refined in shape. Through oxygen plasma etching action or treatment, CNT pillars are transformed to microneedles having micron-size ends to enable an easy and painless skin penetration.

Both direct and remote oxygen plasma treatments can be used to etch the CNT pillars, as long as the etching rate at the top of the pillar is higher than that at the bottom of the pillar. A direct oxygen plasma treatment is preferable when a thick crust layer composed of highly entangled CNT or amorphous carbon presents at the top of the CNT pillars due to its anisotropic etching properties. Once the crust layer has been etched, the top part of the pillar will be etched faster than the bottom part, creating a needle like shape with a sharp tip. A remote oxygen plasma treatment can be used when the crust layer is negligible. Since the etching rate at the top is typically much higher than that at the bottom of the pillar, the final geometry of the etched pillars resembles a sharp tip needle. Depending on the oxygen plasma exposure time or other measure of dosage, the tip and bottom/base diameters of these needles can be varied at the micron scale.

Specifically, the tip and base diameters of the subject needles can be reduced from an original size (typically 30 μm-250 μm) down to a minimum size of a few microns through the oxygen plasma treatment process. Notably, this process is controllable such that intermediate sizes for the tip and base diameter can be achieved. In examples provided, the tip diameter of the needles are reduced by oxygen etching from 50 μm to between about 10 μm and about 1 μm. It is furthermore possible to reduce a hollow CNT pillar of about 10 μm to final tip diameters of under a micron (e.g., about 800 nm) with or without a lumen therein. To be painless in use, the maximum diameter of this subject microneedles maximum diameter is preferably between about 50 μm and about 150 μm, with the length of individual needles between about 175 μm and about 400 μm (preferably about 250 μm).

Invention embodiments include such methodology as broadly presented and as further described. Likewise, embodiments include products produced by such processes. Still further, embodiments include devices including products with the physical characteristics described as well as systems incorporating the same and other features as described and or noted and optionally incorporation by reference. In addition, invention embodiments include methods of use. Such methods of use may comprise methods of drug delivery, of inoculation or vaccination, of analyte acquisition and analysis, etc. Suitable hardware is presented for some of such activity, whereas other hardware is incorporated by reference or would be apparent to those with skill in the art.

BRIEF DESCRIPTION OF THE DRAWINGS

The figures provided herein are diagrammatic and not necessarily drawn to scale, with some components and features exaggerated and/or abstracted for clarity. Variations from the embodiments pictured are contemplated. Accordingly, depiction of aspects and elements in the figures are not intended to limit the scope of the claims, except when explicitly stated as such.

FIGS. 1A-1D are process diagrams for fabricating CNT microneedles with sharp tips from CNT pillars using oxygen plasma etching.

FIGS. 2A-2D illustrate various microneedle array-type devices in which the subject CNT microneedles may be employed.

FIG. 3A is a low magnification image of as-grown CNT pillars with hollow circular cross-section shapes grown on a silicon wafer; FIG. 3B is a high magnification of an as-grown CNT pillar with hollow circle cross-section shapes grown on a silicon wafer.

FIG. 4A is a low magnification image of etched CNT needles after being exposed to 10 minutes oxygen plasma treatment; FIG. 4B is a high magnification image of etched CNT needles after being exposed to 10 minutes oxygen plasma treatment.

FIG. 5A is a low magnification image of etched CNT needles after being exposed to 15 minutes oxygen plasma treatment; FIG. 5B is a high magnification image of etched CNT needles after being exposed to 15 minutes oxygen plasma treatment.

DETAILED DESCRIPTION

Various exemplary embodiments are described below. Reference is made to these examples in a non-limiting sense. They are provided to illustrate more broadly applicable aspects of inventive aspects. Various changes may be made to the invention embodiments described and equivalents may be substituted without departing from its true spirit and scope. In addition, many modifications may be made to adapt a particular situation, material, composition of matter, process, process act(s) or step(s) to the objective(s), spirit or scope of the claims made herein.

Moreover, any of the teachings, techniques and other features described in U.S. Pat. No. 7,955,644 and US Publications 2010/0196446, 2011/0250376, 2012/0021164 and 2012/0058170 referenced above and incorporated herein by reference in their entireties may be employed in connection with the embodiments described herein. Support for any claim may be drawn from these disclosures and specifically set forth herein without adding new matter.

Regarding details of the subject processes and products, FIGS. 1A-1D illustrate fabrications of CNT microneedles with sharp tips from CNT pillars using oxygen plasma etching. Each pillar constitutes a number of individual carbon nano-tubes. The pillar can be a continuous grouping without substantial gaps or can be in a ring-like or annular arrangement with a central channel or lumen, such as for transferring fluid. In FIG. 1A, an array 1000 of a plurality of CNT pillars 100 are provided. These may include a crust layer 102. In any case, the CNTs 100 are shown attached to a substrate 120.

In FIG. 1B, the pillars are exposed to a direct oxygen plasma treatment to provide anisotropic etching. Once the crust layer has been etched, the top part of the pillar will be etched faster than the bottom part, creating a needle like shape with a sharp tip.

Alternatively, in FIG. 1C, a remote oxygen plasma treatment can be used when any crust layer 102 is negligible. Although generally isotropic, since the etching rate at the top is typically much higher than that at the bottom of the pillar, the final geometry of the etched pillars is transformed to that of sharp tip needles 110 such as shown in FIG. 1D.

Depending on the oxygen plasma exposure time/dosage, the tip 112 and bottom/base 14 diameters of needles 110 in an array 1100 can be varied at the micron scale. Moreover, a combination of the processes depicted in FIGS. 1B and 1C is possible.

In any case, needles 110 and needle arrays 1100 so-produced may be employed in a number of ways, examples of which are adapted from those disclosed in US Publication No. 2010/0196446. Such medical applications include uses such as in epidermal or skin patches, eye patches or contact lenses (e.g., synovial eye patches for medicine delivery to aid in cases of near retina sclera and macular degeneration), for colon cancer treatments, dermatology and angioplasty devices to name a handful of options. In such devices, drugs can be introduced to the nanostructures by taking advantage of hydrophobic/hydrophilic properties of certain medicine solutions. Moreover, the properties of particular drugs may be tailored to adjust their hydrophobic/hydrophilic properties to optimize pickup by particular CNT material. Whether used for drug introduction or not, several applications that advantageously employ the sharp-tip CNTs prepared as described herein are illustrated in FIGS. 2A-2D.

In FIG. 2A an epidermal patch 40 to be worn on the skin of a patient/subject is shown. Patch 40 has aligned CNT needles 110 protruding from a substrate 120 in a microneedle array 1100 to be adhered to the skin. A portion of the patch, for example the perimeter of a flexible cover 42 overlaying the substrate/stabilization surface 120, may be coated with adhesive to facilitate releasably securing the device to the skin. When patch 40 is applied to the skin, the CNT microneedles 110 pass through the stratum corneum and enter the viable epidermis to release any drug or agent coated thereon into the skin, essentially painlessly. Alternatively, the CNT needles may include/incorporate a lumen used for drug delivery and the substrate differ, for example, as in other embodiments described below.

Regarding such devices, FIG. 2B illustrates a device 50 including a CNT microneedles array 1100 wherein the microneedles 110 include a lumen therein for injecting a biological agent and/or drawing analyte samples from a patient/subject. Here, the microneedles 110 are secured via anchoring sections 116 embedded in and in fluid communication with a porous polymer matrix substrate 122. For injection, the porous substrate 122 is pre-loaded with an agent, for example, medication, which may then be delivered via the carbon nanotube-based needle into the sub-dermal region. For drawing blood or interstitial fluids, needles 110 transport fluid into the porous substrate.

As another option, the needles may pass through the substrate and be exposed on the other side of the substrate. In which case they may be open to a reservoir defined by a pressurized or flexible bladder wall 52 attached thereto. (Notably, such a needle arrangement relative to a substrate is shown in FIG. 2C.) Other possible overall device configurations shown in U.S. Pat. No. 8,257,324 assigned to Georgia Tech Research Corp. and incorporated herein by reference in its entirety.

Again referring to FIG. 2C, it illustrates a section of an analyte monitoring/sensing device 60 in which CNT microneedles 110 are coupled to a sensor 62 to function as a probe to monitor blood glucose levels or other blood or body fluid properties, for example pH, sugar level, oxygen content, etc. Such a device may function based on the inherent electrical conductivity of the CNTs or it may operate by drawing analyte into the sensor region of the device. In the former case, the CNTs anchored by the substrate 124 may be electrically isolated from one another therein. In the latter case, a fluid transfer section 118 of the microneedles 110 will be in fluid communication with active sensor element(s). Any sensor 62 used may include both onboard and/or separate electronics communicating continuously or intermittently by any of a variety of wireless protocol as well known in the art.

In yet another example, FIG. 2D illustrates an angioplasty device 70 with a balloon 72 at the end of a shaft 74. More specifically, the balloon is shown inflated and bearing the subject sharp-tip microneedles 110 upon substrate material 126 for delivering an anti-hyperproliferation drug (e.g. paclitaxel) following the inflation of the balloon to open a section of a blood vessel. Alternatively, such a balloon (or another structure) could employ the subject microneedles for delivering any of a variety of substances to various parts of the body, including, but not limited to, the skin, uterus, bronchial tubes, and various portions of the gastrointestinal tract including colon.

The construction of this device, the other examples provided above and still others are provided in connection with US Patent Application No. 2010/0196446 noted above, and further details may be drawn from any of U.S. Pat. No. 7,955,644 and US Publications 2011/0250376, 2012/0021164 and 2012/0058170 all of which are incorporated by reference herein in their entireties for all purposes.

CNT MICRONEEDLE FABRICATION EXAMPLES

Patterned CNT pillars were fabricated on a silicon wafer using fabrication process described elsewhere (Bronikowski M. CVD growth of carbon nanotube bundle arrays. Carbon. 2006, 44, 2822-32; Hart A; Slocum A. Rapid growth and flow-mediated nucleation of millimeter-scale aligned carbon nanotube structures from a thin-film catalyst. The journal of physical chemistry B. 2006, 110, 8250-7). Pillars with diameter of less than 50 µm are desirable as shown in FIGS. 3A-B. Subsequently, micron-size CNT needles with sharp tips were fabricated from these pillars by exposing them in oxygen plasma treatment as variously described herein. SEM images typical of the resulting CNT needles after being exposed to a remote oxygen plasma treatment for 10 and 15 minutes at a flow rate of 150 sccm, a pressure of 500 mtorr and a RF power of 50 W to define overall plasma treatment condition dosage are shown in FIGS. 4A-B and 5A-B, respectively.

Microneedle Pillar Fabrication

FIG. 3A is a low magnification image of as-grown CNT pillars with hollow circle cross-section shapes grown on a silicon wafer. These pillars have outer and inner diameters of 50 µm and 25 µm respectively, with spacing of 200 µm and typical length of 500-800 µm. FIG. 3B is a high magnification of an as-grown CNT pillar with hollow circle cross-section shapes grown on a silicon wafer. This pillar has outer and inner diameters of 50 µm and 25 µm respectively.

Sharp Tip Processing

Example I

FIG. 4A is a low magnification image of etched CNT needles after being exposed to 10 minutes oxygen plasma treatment at the prestated dosage conditions. These pillars have tip and bottom diameters of 10 µm and 50 µm respectively, with spacing of 200 µm and typical length of 500-800 µm. FIG. 4B is a high magnification image of one of the etched CNT needles from FIG. 4A. This needle has outer and inner tip diameters of about 6 µm and about 4 µm respectively.

Sharp Tip Processing

Process Example II

FIG. 5A is a low magnification image of etched CNT needles after being exposed to 15 minutes oxygen plasma treatment at the prestated dosage conditions. These pillars have tip and bottom diameters of 1 µm and 20 µm respectively, with spacing of 200 µm and typical length of 500-800 µm. FIG. 5B is a high magnification image of one of the etched CNT needles from FIG. 5A. This needle has an outer tip diameter of about 1 µm and inner tip diameter on the sub-micron length scale or altogether closed-off.

Variations

It is contemplated that any optional feature of the embodiment variations described may be set forth and claimed independently, or in combination with any one or more of the features described herein. Reference to a singular item, includes the possibility that there is a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall avow for the inclusion of any additional element irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity.

The breadth of the present inventive subject matter is not to be limited to the examples provided and/or the subject specification, but rather only by the scope of the claim language. All references cited are incorporated by reference in their entirety. Although the foregoing embodiments been described in detail for purposes of clarity of understanding, it is contemplated that certain modifications may be practiced within the scope of the appended claims.

The invention claimed is:

1. A method of sharp-tip carbon nanotube needle array fabrication, comprising:
exposing a plurality of carbon nanotube pillars in an array to oxygen plasma treatment, wherein the oxygen plasma treatment etches each pillar into a needle shape with a reduced diameter tip relative to a larger diameter base.

2. The method of claim 1, wherein the oxygen plasma treatment is continued until at least some of the needles have a tip diameter of about 10 μm or less.

3. The method of claim 2, wherein a diameter of the pillars before oxygen plasma treatment is at least about 25 μm.

4. The method of claim 3, wherein the pillar diameter before oxygen plasma treatment is about 50 μm.

5. The method of claim 4, wherein the tip diameter produced after oxygen plasma treatment is about 10 μm and the base diameter after oxygen plasma treatment is about 50 μm.

6. The method of claim 4, wherein the tip diameter produced after oxygen plasma treatment is about 5 μm.

7. The method of claim 6, wherein the tip has an outer diameter of 6 μm and an inner diameter of 4 μm.

8. The method of claim 2, wherein the tip diameter produced after oxygen plasma treatment is about 5 μm or less.

9. The method of claim 8, wherein the tip diameter produced after oxygen plasma treatment is about 1 μm or less.

10. The method of claim 9, wherein the tip diameter is about 800 nm.

11. The method of claim 10, wherein the tip includes a sub-micron size lumen.

12. The method of claim 11, wherein the tip includes no lumen.

13. The method of claim 2, wherein the tip includes no lumen.

14. The method of claim 2, wherein the oxygen plasma treatment is a remote treatment.

15. The method of claim 14, wherein the oxygen plasma treatment is dosed at a flow rate of 150 sccm, a pressure of 500 mtorr and a RF power of 50 W for between about 10 and about 15 minutes.

16. The method of claim 1, wherein the oxygen plasma treatment is a direct relative treatment.

* * * * *